US006399107B1

(12) United States Patent
Kessler et al.

(10) Patent No.: US 6,399,107 B1
(45) Date of Patent: Jun. 4, 2002

(54) USE OF INHIBITORS OF GAG SYNTHESIS FOR THE TREATMENT OF CORNEAL HAZE

(75) Inventors: Timothy L. Kessler, Dallas, TX (US); Jon C. Nixon, Belhaven, NC (US); Karen C. David, Mansfield; Gustav Graff, Cleburne, both of TX (US)

(73) Assignee: Alcon Laboratories, Inc., Ft. Worth, TX (US)

( * ) Notice: Subject to any disclaimer, the term of this patent is extended or adjusted under 35 U.S.C. 154(b) by 0 days.

(21) Appl. No.: 09/868,741

(22) PCT Filed: Dec. 13, 1999

(86) PCT No.: PCT/US99/29667

§ 371 (c)(1),
(2), (4) Date: Jun. 20, 2001

(87) PCT Pub. No.: WO00/37072

PCT Pub. Date: Jun. 29, 2000

Related U.S. Application Data

(60) Provisional application No. 60/113,788, filed on Dec. 22, 1998.

(51) Int. Cl.$^7$ .......................... A61K 33/26; A61K 31/35
(52) U.S. Cl. ........................ 424/646; 514/456; 514/912
(58) Field of Search .......................... 424/646; 514/456, 514/912

(56) References Cited

U.S. PATENT DOCUMENTS

| | | | |
|---|---|---|---|
| 4,343,794 A | 8/1982 | Podos et al. | 424/131 |
| 4,665,913 A | 5/1987 | L'Esperance, Jr. | 128/303.1 |
| 4,732,148 A | 3/1988 | L'Esperance, Jr. | 128/303.1 |
| 4,856,513 A | 8/1989 | Muller | 128/303.1 |
| 4,939,135 A | 7/1990 | Robertson et al. | 514/179 |
| 4,941,093 A | 7/1990 | Marshall et al. | 364/413.01 |
| 5,124,392 A | 6/1992 | Robertson et al. | 524/427 |
| 5,271,939 A | 12/1993 | Robertson et al. | 424/427 |
| 5,401,509 A | 3/1995 | Robertson et al. | 424/427 |
| 5,401,510 A | 3/1995 | Robertson et al. | 424/427 |
| 5,525,349 A | 6/1996 | Robertson et al. | 424/427 |
| 5,573,775 A | 11/1996 | Robertson et al. | 424/427 |
| 5,580,570 A | 12/1996 | Robertson et al. | 424/427 |
| 5,582,835 A | 12/1996 | Robertson et al. | 424/427 |
| 5,589,184 A | 12/1996 | Robertson et al. | 424/427 |
| 5,665,373 A | 9/1997 | Robertson et al. | 424/427 |

FOREIGN PATENT DOCUMENTS

| | | |
|---|---|---|
| EP | 0 457 295 A2 | 11/1991 |
| WO | 97/46208 | 11/1997 |
| WO | 98/52546 | 11/1998 |
| WO | 99/45920 | 9/1999 |

OTHER PUBLICATIONS

Moller–Pedersen, et al., "Corneal haze development after PRK is regulated by volume of stromal tissue removal," Cornea, vol. 17(6):627–639, 1998.

Moller–Pedersen, et al., "Confocal microscopic characterization of wound repair after photorefractive keratectomy," Investigative Ophthalmology & Visual Science, vol. 39(3):487–501, 1998.

Del Pero, et al., "Human excimer laser lamellar refractive keratectomy—a clinical study," Investigative Ophthalmology & Visual Science (ARVO Annual Meeting Abstract), vol. 29(8):281, 1988.

Gaster, et al., "Excimer laser ablation and wound healing of superficial cornea in rabbits and primates," Investigative Ophthalamology & Visual Science (ARVO Annual Meeting Abstract), vol. 29(4):309, 1988.

Tuft, et al., "Corneal remodeling following anterior keratectomy," Investigative Ophthalmology & Visual Science (ARVO Annual Meeting Abstract), vol. 29(7):310, 1988.

Hersh, et al., "Results of phase III excimer laser photorefractive keratectomy for myopia," Ophthalmology, vol. 104(10):1535–1553, Oct., 1997.

Marshall, et al., Photoblative reprofiling of the cornea using an excimer laser: Photorefractive keratectomy, Lasers in Ophthalmology, vol. 1(1):21–48, 1986.

Fitzsimmons, et al., "Hyaluronic acid in the rabbit cornea after excimer laser superficial keratectomy," Investigative Ophthalmology & Visual Science, vol. 33(11):3011–3016, Oct., 1992.

Jain, et al., "Antioxidants reduce corneal light scattering after excimer keratectomy in rabbits," Lasers in Surgery and Medicine, vol. 17:160–165, 1995.

Bergmann, et al., "The role of fibroblast inhibitors on corneal healing following photorefractive keratectomy with 193–nanometer excimer laser in rabbits," Ophthalmic Surgery, vol. 25(3):170–174, Mar. 1994.

Morlet, et al., "Effect of topical interferon–alpha 2b on corneal haze after excimer laser photorefractive keratectomy in rabbits," Refractive & Corneal Surgery, vol. 9:443–451, Nov./Dec. 1993.

Weiner, "Polymeric drug delivery systems for the eye," Polymeric Site–Specific Pharmacotherapy, Ed., A. J. Domb, John Wiley & Sons, pp. 316–327, 1994.

Buckingham, et al., "Progressive systemic sclerosis (PSS, scleroderma) dermal fibroblasts synthesize increased amounts of glycosaminoglycan," The Journal of Laboratory & Clinical Medicine, vol. 101(5):659–669, 1983.

*Primary Examiner*—Zohreh Fay
(74) *Attorney, Agent, or Firm*—Sally Yeager

(57) ABSTRACT

This invention relates to the compositions and methods for the treatment of corneal haze. The compositions and methods are particularly directed to the use of GAG synthesis inhibitors in the treatment of corneal haze.

5 Claims, No Drawings

USE OF INHIBITORS OF GAG SYNTHESIS FOR THE TREATMENT OF CORNEAL HAZE

This application is a 371 of the PCT/US99/29667 filed on Dec. 13, 1999 and claims priority from provisional application Ser. No. 60/113,788, filed Dec. 22, 1998.

This invention relates to pharmaceutical compositions and methods of treatment for the prevention and treatment of corneal haze. The formation of corneal haze is an artifact resulting from exposure of the cornea to laser irradiation. The methods of the present invention involve the application of compositions to the eye prior to, during and after irradiation.

BACKGROUND OF THE INVENTION

Laser surgical techniques have been developed to ablate or otherwise treat corneal defects without mechanical abrasion. These techniques include photorefractive keratectomy, ("PRK"), phototherapeutic keratectomy ("PTK") in which laser radiation is applied to the cornea with minimal heating effects to ablate or smooth refractive aberrations, and the LASIK procedure which involves slicing a flap from the cornea, directly, laser ablating a portion of the stroma layer, and replacing the corneal flap.

These techniques involve the use of a pulsed laser photoablation apparatus to ablate very thin layers of corneal tissue with greater precision than can typically be achieved with mechanical means. Such procedures are usually performed with a high energy excimer laser (lasers based on the excited state of a halogen atom combining with the ground state of a rare gas such as krypton or xenon) which emits ultraviolet ("UV") laser radiation capable of ablating biological tissues without thermal damage to surrounding tissue. The laser photoablation procedures typically employ a beam shaping or masking apparatus which varies the size of the exposure area on the corneal surface and interior over time or provides a predefined profile of resistance to the laser radiation, such that areas of the cornea receive different cumulative exposures and thereby are ablated to varying depths. Thus, portions of the epithelium, Bowman's membrane and stroma layers of the cornea are sculpted to effect the correct refractive properties desired. Excimer laser transepithelial photoablation induces significantly less keratocyte loss than manual epithelial debridement. Photoablation, however, is followed by a more intense inflammatory response and a greater increase in backscattering of light, commonly referred to as "corneal haze," that is associated with increased keratocyte activation and myofibroblast transformation. The magnitude of corneal wound repair and the development and duration of corneal haze appears to increase proportionally with in creasing stromal photoablation depth (ice., the volume of stromal tissue removal) and may be unrelated to depth of initial keratocyte loss (Moller-Pedersen et al., Corneal haze development after PRK is regulated by volume of stromal tissue removal. *Cornea*, volume 17, pages 627–639 (1998)).

Corneal haze, as discussed herein, is an artifact which has not been observed as a result of ophthalmic surgery until the advent of these laser photoablation procedures. The artifact is seen as opacification of the cornea, or a "cloudiness" in vision. The artifact resulting from laser surgery is seen in different parts of the cornea but particularly in the stroma. When the artifact does appear it can usually only be observed by use of a slit lamp. It is not known precisely why the artifact sometimes occurs after photoablation of the cornea. It is hypothesized that the development of clinically observed corneal haze in PRK patients may be related, in part, to activation of corneal keratocytes and to putative changes in the extracellular matrix (Moller-Pedersen et al., Confocal microscopic characterization of wound repair after photorefractive keratectomy, *Invest. Ophthalmol. Vis. Sci.*, volume 39, pages 487–501 (1998)). The development of corneal haze is of potentially greater concern in those procedures affecting a large surface of the cornea versus procedures involving laser incisions.

The corneal haze or artifact to be prevented or treated according to the present invention is not a result of the use of lasers in the work area. It is rather a result of purposeful and direct exposure of the cornea to surgical trauma especially that of laser irradiation during ophthalmic surgery. Recent studies have been performed regarding the corneal haze which results from exposure to lasers. For example, in one study, seven patients received laser corneal ablation with a 193 nm Questek excimer laser. Post ablation examination with a slit beam showed a speckled haze at the interface between the epithelium and stroma (Del Pero, et al., Human Excimer Laser Lamellar Refractive Keratectomy—A Clinical Study, *ARVO Annual Meeting Abstract Issue,* page 281, No. 8 (1988)). In another study ablation with a 193 nm excimer laser resulted in a slight haze in the corneas of rabbits and primates. The haze was observable by slit lamp but disappeared after two weeks. However, in the rabbits a material resembling a plasma membrane was reported in Descemet's membrane, which is located between the posterior surface of the stroma and the anterior surface of the corneal endothelium (Gaster et al., Excimer Laser Ablation and Wound Healing of Superficial Cornea in Rabbits and Primates. *ARVO Annual Meeting Abstract Issue,* page 309, No. 4 (1988)). In another study discs were formed in the corneal stromas of rabbits by excimer laser photoablation at 193 nm. A stromal haze developed by one month, but corneal transparency did improve after 6 months (Tuft et al., Corneal Remodeling Following Anterior Keratectomy, *ARVO Annual Meeting Abstract Issue,* page 310, No. 7 (1988)). In a recent Phase III study on the use of excimer laser PRK for treatment of myopia, 27.8% of the 701 patients undergoing the surgical procedure demonstrated detectable haze formation (Hersh et al., Results of phase III excimer laser photorefractive keratectomy for myopia. The Summit PRK Study Group, *Ophthalmology,* volume 104, pages 1535–1553 (1997)). There exists, therefore, a need to provide methods of treatment to prevent the appearance of and/or treat corneal haze induced by laser irradiation.

For further details on PRK techniques, see Marshall et al., Photo-ablative Reprofiling Of The Cornea Using An Excime, Laser: Photorefractive Keratectomy, volume 1, *Lasers in Ophthalmology,* pages 21–48 (1986) and U.S. Pat. No. 4,856,513 (Muller), U.S. Pat. No. 4,941,093 (Marshall, et. al.), U.S. Pat. No. 4,665,913 (L'Esperance) and U.S. Pat. No. 4,732,148 (L'Esperance) all of which are incorporated herein by reference to the extent that they disclose methods and devices for achieving a predetermined refractive correction by volumetric removal of corneal tissue.

U.S. Pat. Nos. 5,665,373, 5,589,184, 5,582,835, 5,580,570, 5,573,775, 5,525,349, 5,401,510, 5,401,509, 5,271,939, 5,124,392 and 4,939,135, all issued to Robertson et al., disclose compositions and methods for the treatment of post-laser surgery corneal haze. None of these patents, however, disclose the compositions or methods of the present invention.

SUMMARY OF THE INVENTION

The present invention is directed to compositions and methods for treating corneal haze. The compositions comprise inhibitors of glycosaminoglycan ("GAG") synthesis.

The compositions containing the GAG synthesis inhibitors are formulated as solutions, suspensions, emulsions or gels depending on the characteristics of the particular inhibitor. The compositions can also be delivered via use of a collagen shield, contact lenses or other solid matrixes capable of delivering drugs to the cornea when placed on the ocular surface.

The compositions and/or methods of the present invention may also involve the use of adjunctive agents, e.g., antiinfectives or antiinflammatories, to aid the wound healing process.

The compositions are used to prevent or treat corneal haze and are applied to the eye prior to and/or during surgical exposure to laser radiation and/or postoperatively.

DETAILED DESCRIPTION OF THE INVENTION

The present invention is directed to compositions and methods of use for the treatment of corneal haze resulting from laser irradiation of the eye. The compositions of the present invention comprise GAG synthesis inhibitors. As used herein, "GAG synthesis inhibitor" refers to compounds that inhibit the synthesis/formation of GAGs. Regardless of any theory of mechanism, the GAG synthesis inhibitors of the present invention facilitate the prevention or reduction of corneal haze. As used herein, "corneal haze" refers to the clouding of the cornea which results from exposure of the cornea to laser radiation during eye surgery. The compositions comprising the GAG synthesis inhibitors are useful for the prevention and treatment of corneal haze resulting from laser irradiation of the cornea.

Without intending to be bound by any theory, it is believed that corneal haze results from the formation of keratocyte (corneal stromal fibroblasts) vacuoles containing GAGs and/or newly synthesized collagen fibers. In the post-corneal wounding (PRK) rabbit model, re-epithelialization is completed in less than a week. Stromal haze appears around two weeks and peaks by eight weeks following wounding (See generally, Fitzsimmons et al., Hyaluronic Acid in the Rabbit Cornea After Excimer Laser Superficial Keratectomy, *IVOS*, volume 33, pages 3011–3016 (1992); Jain et al., Antioxidants Reduce Corneal Light Scattering After Excimer Keratectomy in Rabbits. *Lasers in Surgery and Medicine*, volume 17, pages 160–165 (1995); Bergman et al., The Role of Fibroblast Inhibitors on Corneal Healing Following Photorefractive Keratectomy With 193-Nanometer Excimer Laser in Rabbits. *Ophthalmic Surgery*, volume 25, pages 170–174 (1994); Morlet et al., Effect of Topical Interferon-Alpha 2b on Corneal Haze After Excimer Laser Photoreferactive Keratectomy in Rabbits. *Refract. Corneal Surgery*, volume 9, pages 443–451 (1993).) During this period, fibroblasts migrate into the wound area and secrete new extracellular matrix including high concentrations of GAGs. Over the next several (approximately 3–6) months there is a decline in the number of activated fibroblasts and the haze is gradually reduced. Thus, the present inventors believe that high GAG concentration in the cornea following laser irradiation leads to corneal haze.

It has been discovered by the present inventors that the cytokines. IL-1 and TGFb, induce/stimulate the synthesis of GAGs in human corneal fibroblasts.

Examples of GAG synthesis inhibitors include phosphatase inhibitors and protein kinase inhibitors. Phosphatase inhibitors inhibit the phosphate hydrolysis function of phosphatase enzymes. Protein kinase inhibitors inhibit the protein activation or deactivation function of protein kinases.

Particular protein kinases, such as the tyrosine kinase inhibitors, may have specific utility in the methods of the present invention. Tyrosine protein kinase inhibitors inhibit the tyrosine-protein activation or deactivation function of tyrosine kinases. Examples of the above inhibitors are listed in Table 1:

TABLE 1

Protein Kinase Inhibitors

1. N-(2-aminoethyl)-5-isoquinolinesulfonamide
2. Bisindolylmaleimide I
3. Chelerythrine chloride
4. 1-(5-chloronaphthalene-1-sulfonyl)-1H-hexahydro-1,4-diazepine
5. Dl-dihydrosphingosine
6. Rac-2-ethoxy-3-hexadecanamido-1-propyl phosphocholine
7. GF 109203X
8. Hexadecyl phosphocholine
9. 1-(5-iodonaphthalene-1-sulfonyl)-1H-hexahydro-1,4-diazepine
10. 1-(N,O-bis-[5-isoquinolinesulfonyl]-N-methyl-1-tyrosyl)-4-phenylpiperazine
11. 1-(5-isoquinolinylsulfonyl)-2-methylpiperazine
12. 1-(5-isoquinolinylsulfonyl)piperazine
13. KN-93
14. Rac-2-methoxy-3-hexadecanamido-1-propyl phosphocholine
15. Rac-2-methoxy-3-octadecanamido-1-propyl phosphocholine
16. N-(2-[methylamino]ethyl)-5-isoquinolinesulfonamide
17. Palmitoyl-dl-carnitine chloride
18. D-erythro-sphingosine
19. Staurosporine
20. Dl-stearoylcarnitine chloride
21. Tamoxifen
22. 3,4,5-trimethoxybenzoic acid 8-(diethylamino)octyl ester
23. Arg-lys-arg-ala-arg-lys-glu
24. Protein kinase A inhibitor fragment 6–22 amide
25. Protein kinase C fragments
26. Autocamtide-2-related inhibitory peptide Tyrosine Kinase Inhibitors 1. Lavendustin A
2. Piceatannol
3. Tyrphostin AG
4. 5-(2,5-dihydroxybenzylamino)-2-hydroxybenzoic acid
5. 2,5-dihydroxycinnamic acid methyl ester
6. Genistein
7. Herbimycin A
8. Lavendustin B
9. Tyrphostin Phosphatase Inhibitors 1. Microcystin LR
2. Protein phosphatase inhibitor-2
3. Calyculin A
4. Dimethyl-dl-2,3-distearoyloxypropyl(2-hydroxyethyl) ammonium acetate
5. Okadaic acid
6. Okadaic acid methyl ester The above GAG synthesis inhibitors may be obtained commercially, purified from natural sources, or prepared by synthetic methods known to those skilled in the art.

The GAG synthesis inhibitors of the present invention may be applied alone or in combination with other GAG synthesis inhibitors. In addition, individual GAG synthesis inhibitors or combinations thereof may be applied together, sequentially or offset from each other, e.g., dosing a GAG synthesis inhibitor in the morning and dosing another in the evening. The particular dose and treatment regimen, however, are left to the discretion of the clinician.

The GAG synthesis inhibitors which can be used to prevent or alleviate corneal haze are formulated in compositions for topical application to the eye. The preparation of topical ophthalmic compositions is well known in the art. Generally, topical ophthalmic compositions useful in the present invention will be in the form of a solution, suspension, gel, or formulated as part of a device, such as a collagen shield or other bioerodible or non-bioerodible device. Various excipients may be contained in the topical ophthalmic solutions, suspensions or gels of the present invention. For example, buffers (e.g., borate, carbonate, phosphate), tonicity agents (e.g., sodium chloride, potassium chloride, polyols), preservatives (e.g., polyquaterniums, polybiguanides, BAC), chelating agents (e.g., EDTA), viscosity enhancing agents (e.g., polyethoxylated glycols) and solubilizing agents (e.g., polyethoxylated castor oils, including polyoxl-35 castor oil (Cremophor EL®, BASF Corp., Parsippany, N.J.); Polysorbate 20, 60 and 80; Pluronic® F-68, F-84 and P-103 (BASF Corp.); or cyclodextrin) may be included in the topical ophthalmic compositions. However, preferable compositions of the present invention will not include preservatives or tonicity agents which are known to adversely affect or irritate the eye, particularly the cornea.

A variety of gels may be useful in topical ophthalmic gel compositions of the present invention, including, but not limited to, carbomers, polyvinyl alcohol-borates complexes, or xanthan, gellan, or guar gums. Topical ophthalmic bioerodible and non-bioerodible devices are known in the art and may be useful in the topical administration of the GAG synthesis inhibitors. See, for example, Weiner, A. L., Polymeric Drug Delivery Systems For the Eye, in *Polymeric Site-specific Pharmacotherapy*, Ed., A. J. Domb, John Wiley & Sons, pages 316–327 (1994). While the particular ingredients and amounts to be contained in topical ophthalmic compositions useful in the methods of the present invention will vary, particular topical ophthalmic compositions will be formulated to effect the administration of one or more GAG synthesis inhibitors topically to the eye.

As will be understood by those skilled in the art, the administration, sequence of administration when more than one GAG synthesis inhibitors are used, and the concentrations of the GAG synthesis inhibitors used depends on numerous factors. These factors can include: the specific GAG synthesis inhibitor or inhibitors being used, the nature of the surgical procedure, and various clinical factors, including the extent and type of corneal haze being treated, the medical history of the patient, symptoms apparent prior to, during, or after surgery, such as inflammation or edema, etc. Selection of specific GAG synthesis inhibitors or combinations thereof, their concentrations and sequence of delivery to the eye will be made by the skilled clinician guided by the forgoing description.

In general, the doses of GAG synthesis inhibitors used for the above described purposes will vary, but will be in an effective amount to prevent, reduce or ameliorate corneal haze. As used herein, "pharmaceutically effective amount" refers to that amount of one or more GAG synthesis inhibitors which prevents, reduces or ameliorates corneal haze. The GAG synthesis inhibitors will normally be contained in the compositions described herein in an amount from about 0.01 to about 2.0 percent weight/volume ("% w/v"). The compositions of the present invention may be delivered topically to the cornea, about one to six times a day, prior to, during and/or following laser surgery.

As used herein, the term "pharmaceutically acceptable vehicle" refers to any formulation which is safe, and provides the appropriate delivery for the desired route of administration of an effective amount of at least one GAG synthesis inhibitor of the present invention.

Regardless of the reason or combination of reasons for development of corneal haze, there are compounds, or compositions, collectively referred to herein as "adjuncts" which can be used alone, or in addition to the GAG synthesis inhibitors discussed above, that contribute to the overall health and comfort of the eye, thus contributing to the prevention of corneal haze and its treatment.

For example, during and following photoablation of the cornea, elevation of intraocular pressure ("IOP") may occur. Control of intraocular pressure contributes to the health of the cornea thereby allowing the cornea to heal without resulting corneal haze. Adjuncts for controlling intraocular pressure which can be used in combination with GAG synthesis inhibitors include agents which lower IOP. IOP lowering agents which can be used include, for example, prostaglandins or prostanoids, carbonic anhydrase inhibitors, beta-adrenergic agonists and antagonists, alpha-adrenergic agonists or other IOP lowering agents known to those skilled in the art. Such compounds can be topically applied to the eye following photoablation at concentrations between about 0.1 and 2.0 % (w/v) preferably about 0.5 % (w/v). In addition, miotics can be used to control intraocular pressure. For example miotics such as carbachol, pilocarpine, physostigmine, echothiophate and isofluorphate can be used.

Humectants may be used prior to, during and after photoablation of the cornea. These adjuncts promote healing of the cornea by providing lubrication and preserving the natural tear physiology. Humectants can include preparations which typically comprise hydroxyethylcellulose, hydroxypropylcellulose, hydroxypropylmethylcellulose, methylcellulose, polyvinyl alcohol, cellulose esters, povidone or other suitable polymeric systems.

Epithelial cell health promoters as used herein, are compounds known to contribute to the health of the epithelial cells of the cornea. The presence of these compounds prior to, during, and/or after photoablation of the cornea can contribute to the prevention of corneal haze by encouraging the rapid resumption of epithelial integrity and prevention of stromal edema. Epithelial cell health promoters which can be used as adjuncts to the GAG synthesis inhibitors of the present invention can include: ascorbic acid; retinoids, such as retinoic acid, retinol, retinal and retinoyl B-glucuronide; aloe vera; collagenase inhibitors; prostaglandins, such as prostaglandin E and elastase inhibitors.

PRK and PTK photoablation leaves the cornea denuded of its protective epithelial layer leaving it prone to infection. Antimicrobials can be used according to the present invention preoperatively and post-operatively thereby safeguarding against corneal infection which inhibits healing, possibly leading to corneal edema and the formation of corneal haze. Antimicrobials which can be used according to the present invention include: chloramphenicol, erythromycin, gentamycin, polymyxin, sulfacetamide, tetracycline, tobramycin, sulfisoxazole, diolamine, ciprofloxacin, natamycin, neomycin, ofloxacin, norfloxacin, trifluorothymidine, acyclovir, gancyclovir, vancomycin and other antibacterial, antiviral and antifungal agents. The compositions comprise one or more antimicrobials or combinations of antimicrobials and other GAG synthesis inhibitors. Such antimicrobials are used at concentrations between about 0.05 and 3.0 % (w/v), and preferably less than about 1.0 % (w/v).

As stated above, the present invention also encompasses methods of treatment of an eye exposed to laser radiation during ophthalmic procedures. Methods of treatment, during ophthalmic surgery, with compositions containing GAG synthesis inhibitors, as disclosed above, include application of the compositions before laser exposure, during the procedures, for example when the eye is moistened and a wet keratoscope reading is taken during corneal sculpting using a laser and/or immediately after irradiation. In addition, and as previously discussed, the compositions of the present invention can be applied uniquely or when the use of more than one GAG synthesis inhibitor is indicated, the medicaments can be administered sequentially.

The following formulations are examples of a GAG synthesis inhibitor compositions that may be used for the prevention and treatment of corneal haze resulting from laser irradiation. They are not limiting but considered representative of useful compositions of the present invention.

EXAMPLE 1

Topical compositions useful for treating corneal haze:

| Component | % (w/v) |
|---|---|
| GAG synthesis inhibitor | 0.01 to 2.0 |
| Tyloxapol | 0.01 to 0.05 |
| HPMC | 0.5 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. |

EXAMPLE 2

A preferred topical composition useful for treating corneal haze:

| Component | % (w/v) |
|---|---|
| GAG synthesis inhibitor | 0.01 to 2.0 |
| Tyloxapol | 0.01 to 0.05 |
| HPMC | 0.5 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. |

EXAMPLE 3

Preferred formulation for a topical ocular solution:

| Component | % (w/v) |
|---|---|
| GAG synthesis inhibitor | 0.01 to 2.0 |
| Benzalkonium chloride | 0.01% |
| HPMC | 0.5% |
| Sodium chloride | 0.8% |
| Sodium phosphate | 0.28% |
| Edetate disodium | 0.01% |
| NaOH/HCl | q.s. pH 7.2 |
| Purified Water | q.s. 100 mL |

The formulations of Examples 1–3, above, can be made by methods known in the art.

EXAMPLE 4

This example demonstrates the efficacy of GAG synthesis inhibitors of the present invention on the inhibition of glucosamine incorporation in GAGs:

The assay was performed as follows:

A. Cell Culture

Primary human corneal fibroblasts were seated in Costar 24-well plates at 8,000 cells/well. Corneal fibroblasts were cultured to 90% confluency in Hams F-10 medium supplemented with heat inactivated fetal bovine serum (10%), penicillin (100 U/ml), streptomycin (100 µg/ml) and 2 mM L-glutamine in a humidifed incubator at 37° C. in 5% $CO_2$/95% air. Cultures were then exposed to 0.1% serum containing-medium with 0.1% DMSO or GAG synthesis inhibitor (DMSO vehicle) for 30 minutes at 37° C. GAG synthesis was then assessed by further incubating the cells with the addition of [3H]glucosamine (5.0 µCi/mL) in the presence or absence of IL-1B (10 ng/mL), TGFβ2 (1 ng/mL) or $PGE_2$ (1 µM) for 48 hours, at which time medium was removed and centrifuged (14,000 rpm) for 3 minutes.

B. GAG Measurement

The method previously described by Buckingham et al., *J. Lab Clin Med.* Volume 101, pages 659–669 (1983)) was followed for GAG measurement. After the [3H]glucosamine incubation, medium was removed from each well and placed into separate tubes. (Optionally, if necessary, the cultures were centrifuged to remove cellular debris/particulate matter). The medium were incubated with 0.2 ml of 0.1 M Tris buffer, pH 8.0, containing 10 mg/ml Protease (Sigma) for 4 hours at 55° C. Carrier GAG (50 µl of GAG solution containing hyaluronic acid (5 mg/ml) and chondroitin sulfate (5 mg/ml) (250 µg each)) was added to each sample, followed by 8 mL of 0.5% CPC in 0.002 M $Na_2SO_4$. Reaction tubes were mixed and allowed to stand for 20 minutes at room temperature. The precipitates were collected on Whatman glass fiber filters (GF/F). Individual tubes and filters were washed with 10 mL 0.1% CPC in 0.05 M NaCl and then washed with 20 mL distilled water. They were then placed in liquid scintillation counting vials and 5 mL of Opti-fluor was added and counted in a Rackbeta liquid scintillation counter.

Protein Determination

After the 48 hour incubation, unstimulated-unlabeled culture medium removed and cells solubilized in 100 µl of 0.1 N NaOH. Protein determination by the BCA Protein method.

The results are illustrated in Table 2, as $IC_{50}$'s (i.e., concentration giving 50% inhibition of GAG synthesis) of the various GAG synthesis inhibitors versus various GAG synthesis stimulators.

TABLE 2

Effect Of GAG synthesis inhibitors on IL-1B-, TGFβ- and $PGE_2$-Induced ³H-Glucosamine Incorporation into Glycosaminoglycans

| | | GAG Synthesis Stimulator | | |
|---|---|---|---|---|
| Agent | Inhibitor Class/Target | IL-1B | TGFβ | $PGE_2$ |
| | | Inhibition ($IC_{50}$ (µM)) | | |
| Genistein | TK Inhibitor | 45.63 | 55.91 | 70.89 |
| $NaVO_3$ | Phospliatase Inhibitor | 19.9 | 67.2 | 10.5 |
| Staurosporine | PK Inhibitor | 0.0104 | 0.0132 | 0.0011 |
| Mannose 6-Phosphate | Latent TGFβ Inhibitor | >10,000 | 23.3 | >10,000 |

The invention in its broader aspects is not limited to the specific details shown and described above. Departures may be made from such details within the scope of the accompanying claims without departing from the principles of the invention and without sacrificing its advantages.

We claim:

1. A method for the treatment of corneal haze which comprises administering to a human patient prior to, during or after corneal laser surgery, or combinations thereof, one or more compositions comprising an effective amount of one or more GAG synthesis inhibitor(s) and a pharmaceutically acceptable vehicle.

2. A method according to claim 1, wherein the GAG synthesis inhibitor is/are genistein, $NaVO_3$ or staurosporine, or combinations thereof.

3. A method according to claim 1, wherein the composition is a topical ophthalmic composition.

4. A method according to claim 2, wherein the composition is a topical ophthalmic composition.

5. A method according to claim 1, wherein the corneal laser surgery is PRK, PTK or LASIK.

* * * * *